United States Patent
Yates et al.

(10) Patent No.: US 6,702,929 B2
(45) Date of Patent: Mar. 9, 2004

(54) PURIFICATION OF 1,1,1,3,3-PENTAFLUOROBUTANE

(75) Inventors: Stephen Frederic Yates, Arlington Heights, IL (US); Hsueh Sung Tung, Getzville, IL (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/337,836

(22) Filed: Jan. 7, 2003

(65) Prior Publication Data

US 2003/0111332 A1 Jun. 19, 2003

Related U.S. Application Data

(63) Continuation of application No. 09/737,378, filed on Dec. 15, 2000, now abandoned.

(51) Int. Cl.$^7$ .......................... C07C 17/00; C01B 63/00; C07B 63/00
(52) U.S. Cl. ........................... 204/157.94; 204/157.95; 204/158.11; 204/158.2; 204/158.21
(58) Field of Search ..................... 204/157.94, 157.95, 204/158.11, 158.21, 158.2

(56) References Cited

U.S. PATENT DOCUMENTS

| | | |
|---|---|---|
| 5,917,098 A | 6/1999 | Bertocchio et al. |
| 5,944,962 A | 8/1999 | Boyce |
| 2002/0125122 A1 | 9/2002 | Braun et al. |

FOREIGN PATENT DOCUMENTS

| | | |
|---|---|---|
| DE | 100 29 283 A1 | 12/2000 |
| WO | WO 97/37955 | 10/1997 |

*Primary Examiner*—Johann Richter
*Assistant Examiner*—Eluis O. Price
(74) *Attorney, Agent, or Firm*—Colleen D. Szuch

(57) ABSTRACT

In the synthesis of 1,1,1,3,3-pentafluorobutane (R-365mfc), a mixture of R-365mfc and the impurity 1,1,1,3-tetrafluoro-2-butene (R-1354mzy) is purified and R-1354mzy is removed from the mixture by contacting the mixture with 1–5 mols of chlorine for each mol of R-1354mzy in the presence of ultraviolet light having a wavelength between about 300 to 400 nm which provides at least 0.02 watts-hour/kg of the mixture. The R-1354mzy is reduced to below 10 wt. ppm as it is converted to 2,3-dichloro-1,1,1,3-tetrafluorobutane (R-354) or other butane containing more chlorine and having a higher boiling point than R-365mfc. The butane(s) may be separated more easily from R-365mfc. The photochlorination is effected in a manner such that at least about 96 weight percent of the starting amount of R-365mfc is maintained in the mixture.

11 Claims, No Drawings

PURIFICATION OF 1,1,1,3,3-PENTAFLUOROBUTANE

CROSS-REFERENCE TO RELATED APPLICATIONS

This is a continuation application of U.S. patent application Ser. No. 09/737,378, filed Dec. 15, 2000, now abandoned.

BACKGROUND OF THE INVENTION

This invention relates principally to the purification of 1,1,1,3,3-pentafluorobutane, also designated R-365mfc, which has been of particular interest as a replacement for chlorofluorocarbons and hydrochlorofluorocarbons having similar physical properties, for example, 1,1,2-trichloro-1,2,2-trifluoroethane (R-113), fluorotrichloromethane (R-11) and 1,1-dichloro-1-fluoroethane (R-141b).

R-365mfc may be prepared by a two-step process involving the addition of carbon tetrachloride to 2-chloropropene to produce 1,1,1,3,3-pentachlorobutane (R-360) in the presence of a copper salt and an amine followed by fluorination with hydrogen fluoride as disclosed in U.S. Pat. No. 5,917,098.

It is characteristic of such reactions that many by-products are formed, containing varying numbers of hydrogen, chlorine, and fluorine atoms on $C_1$–$C_4$ compounds. These by-products and the unreacted feed material may be separated by distillation where possible. Some compounds are relatively harmless since their presence does not greatly alter the physical properties for which R-365mfc is useful. One by-product which must be removed because of its toxicity is 1,1,1,3-tetrafluoro-2-butene (R-1354mzy), although only relatively small amounts are typically present in R-365mfc as formed. R-1354mzy has a boiling point close to that of R-365mfc making them difficult to separate by distillation. After distillation of the crude product, R-1354mzy will still be present in amounts from about 300 to 20,000 wt. ppm. It should be reduced to below about 100 wt. ppm due to the potential toxicity of unsaturated compounds. Preferably, the amount of R-1354mzy should be reduced to 20 ppm (wt.) and most preferably below about 10 wt. ppm.

Further improvement in methods of purifying R-365mfc, particularly with respect to eliminating R-1354mzy, is desired and the present inventors have discovered a means for purification by photochlorination.

It is advantageous also to remove other unsaturated by-products that can be present in the R-365mfc reaction product, including, for example, R-1353 and the like.

SUMMARY OF THE INVENTION

Unsaturated by-products including R-1354mzy are removed from a mixture consisting substantially of R-365mfc and containing up to about 20,000 wt. ppm R-1354mzy by contacting the R-365mfc mixture with 1–5 moles of chlorine for each mole of R-1354mzy in the presence of ultraviolet light having a wavelength between about 300 to 400 nm which provides at least 0.02 watts-hour/kg of the mixture, preferably 0.02 watts-hr/kg of the mixture, preferably 0.02 to 2.0 watts-hour/kg. The R-1354mzy can be reduced to below 10 wt. ppm or lower as it is converted to 2,3-dichloro-1,1,1,3-tetrafluorobutane (R-354) or other butanes containing more chlorine such as 2,2,3-trichloro,1,1,1,3-tetrafluorobutane (R-344) or 2,2,3,4-tetrachloro1,1,1,3-tetrafluorobutane (R-334), which have higher boiling points and can be easily separated from R-365mfc. Other unsaturated compounds, such as 3-chloro-1,1,1-trifluoro-2-butene (R-1353), are also removed by chlorination to other derivatives that can be separated, for example, by distillation. The temperature and pressure used may be adjusted to provide R-365mfc in either the vapor or liquid phase, the vapor phase being preferred.

An advantage of the photochlorination of the present invention is that it does not affect materially the desired R-365mfc product. Thus, while a high proportion of the R-1354mzy impurity is in effect removed by the photochlorination, a substantially high proportion of the R-365mfc is maintained. For example, the photochlorination can be effected in a manner such that at least about 96 weight percent, preferably at least about 98 wt. %, of the starting amount of R-365mfc is maintained in the mixture. This is indeed surprising when it is considered that the proportion of R-365mfc in the starting mixture is high, for example, at least about 98 weight percent.

DETAILED DESCRIPTION

R-365 may be produced by the process of U.S. Pat. No. 5,917,098, beginning from carbon tetrachloride and 2-chloroprene. The crude product will contain a variety of by-products. It is of particular importance to remove 1,1,1,3-tetrafluoro-2-butene (R-1354mzy) from the crude product. Preliminary separation of R-365mfc by distillation will leave about 300 to 20,000 wt. ppm of R-1354mzy having a boiling point of about 16° C. compared to 40° C. for R-365mfc, the difference in boiling points making R-1354mzy difficult to separate from R-365mfc. In the process of the invention, R-1354mzy or other unsaturated compounds which may be present, for example, 3-chloro-1,1,1-trifluoro-2-butene (R-1353), are reacted with chlorine to provide more highly chlorinated compounds which have a higher boiling point and can be readily separated from R-365mfc.

As mentioned above, the photochlorination may be effected so that at least about 96% (based on weight amount) or more of the desired starting amount of R-365mfc is maintained in the mixture, i.e. not affected by the photochlorination.

In the process, crude R-365mfc containing about 300 to 20,000 wt. ppm of R-1354mzy along with minor amounts of other by-products such as those mentioned above will be contacted with chlorine in the presence of ultraviolet light having a wavelength of about 300 to 400 nm. It should be understood that an ultraviolet lamp may have radiation outside this range also, but that photochlorination requires UV light within this range.

The ultraviolet light will have an intensity which provides an exposure greater than zero and at least about 0.02 watts-hour/kg of the R-365mfc mixture, preferably 0.02 to 2.0 watts-hour/kg.

The ultraviolet light may be provided by arc lamps including mercury, argon, or xenon and filament lamps including tungsten and halogen.

Chlorine is introduced into the crude R-365mfc stream at a rate sufficient to provide about 1 to 5 moles of chlorine for each mole of R-1354mzy, preferably about 1 to about 1.5. It has been found that increasing either the ratio of chlorine to R-1354mzy ($Cl_2$/R-1354mzy) or the ultraviolet light exposure improves the chlorination of R-1354mzy. Generally, we have been able to reduce the R-1354mzy to below 10 wt. ppm using a UV exposure above about 0.04 watts-hour/kg but with quite low ratios of $Cl_2$/R-1354mzy. Conversely, much lower UV exposures can be used if higher $Cl_2$/R-1354mzy ratios are used. The $C_2$/R-1354mzy ratio and UV exposure may be adjusted to provide the desired set of conditions.

The temperature employed may vary but may be from about −50° C. to 200° C., preferably about 250 to 60° C.

The pressure selected will be a convenient value to suit the processing conditions for R-365mfc and to assure that R-365mfc is a liquid or vapor as desired.

The UV radiation from a lamp ordinarily will be expressed as watts, which is a rate of delivering energy. For present purposes, it is considered more useful to express radiation as the quantity of energy delivered over a period of time, i.e. the "exposure," rather than as the rate. Thus, the exposure may be expressed as watts-hours, which is related to the number of photons of energy delivered and their wavelength and these, in turn, relate to the chlorination of unsaturated molecules such as R-1354mzy. Since the exposure is the product of the rate of delivering energy (photons/time) and the time, it will be clear that either the rate or the time could be varied. However, for practical applications the rate and the time will have limits imposed by the need to carry out the desired photochlorination reaction within constraints of time and product yield. If a high rate or a long time is used, not only will R-1354mzy be chlorinated to R-354 (or R-344 or R-334), but also chlorine will react with other molecules, particularly with R-365mfc to make 2-chloro-1,1,1,3,3-pentaflurobutane (R-355mdc). Alternatively, if a very low rate, or a short time, is used then insufficient chlorination of R-1354mzy would be expected. Increasing the ratio of chlorine to R-365mfc will tend to increase the production of R-355mdc. Conditions which involve a UV exposure of about 1.5 to 5.0 watts-hour/kg of R-365mfc and a $Cl_2$/R-1354mzy molar ratio of greater than about 1.5:1 and up to about 50:1 will tend to result in increased production of R-355mdc.

As illustrated in the examples, the photochlorination can be effected in a batch process or a continuous process.

After the R-365mfc-containing mixture has been photochlorinated, the chlorinated products may be separated from the R-365mfc, for example, by distillation, since the boiling points are no longer close to that of R-365mfc.

For example, the boiling points of R-354, R-344, R-334 and other chlorinated butanes that are typically produced in the photochlorination are at least about 40° C. above the boiling point of R-365mfc (40° C.). To exemplify, the boiling points of R-354 isomers are estimated to be about 83° C.; the boiling points of R-344 isomers are estimated to be about 120° C.; and boiling points of R-334 isomers are estimated to be about 155° C. The boiling point of R-355 is estimated to be about 48° C. (The boiling points referred to in this specification are at one atmosphere pressure.) Separation of the Cl-containing by-products can be effected readily by conventional distillation. Any residual chlorine, HCl or HF may be separated by absorption of chlorine in aqueous caustic, by adsorption on carbon molecular sieves, or reaction with aqueous sodium sulfite or sodium thiosulfate.

EXAMPLES

Example 1 Liquid Phase Purification of R-365mfc

The photochlorination of R-365mfc is carried out in a 125 mL Pyrex pressure vessel equipped with a dip leg inlet and a pressure gauge. This vessel is chilled in ice water and 20.0 grams of impure R-365mfc containing 0.08% R-1354mzy is condensed into it. Then, while still cold, a stream of chlorine gas is passed at 10 mL/min through this solution for about 52 seconds. We calculate according to the ideal gas law that this should correspond to $3.6 \times 10^{-4}$ moles of chlorine, or a 1:1 mole ratio with the R-1354mzy impurity. The vessel is then allowed to warm to room temperature.

The reactor vessel is placed for 5 minutes at the focus of RPR-100 Rayonet reactor (Southern New England Ultraviolet Company) equipped with 16 RPR-3500 lamps having their peak intensity at a wavelength of 350 nm. The Pyrex walls of the pressure vessel remove light below 300 nm. Ferrioxalate actinometry is used to measure the radiation received (see *The Chemists Companion*, A. J. Gordon & R. A. Ford, Wiley Interscience (1972), pages 362–368). In this vessel under these conditions this procedure gives an incident light intensity of $1.317 \times 10^{-7}$ Einstein/sec (0.0417 watts). One Einstein is equal to a mol of photons. A five minute exposure should therefore supply $3.95 \times 10^{-5}$ Einsteins of light (0.039 watt-hour/kg). After exposure, the vapor head of the pressure vessel is sampled by gas chromatography.

Example 2 Vapor Phase Purification of R-365mfc

The photochlorination of R-365mfc is carried out in a 125-mL Pyrex pressure vessel equipped with an inlet at the bottom and an outlet at the top. The reactor vessel is placed at the focus of RPR-100 Rayonet reactor (Southern New England Ultraviolet Company) equipped with 16 RPR-3500 lamps having their peak intensity at a wavelength of 350 nm. The Pyrex walls of the pressure vessel remove light below 300 nm. The vessel is immersed in a Pyrex constant temperature bath held at 59° C. to ensure that the R-365mfc remains in the vapor phase.

Two feed streams are passed through separate lengths of capillary tubing and then mixed and passed into the reactor at 5 psig (34.5 kPa gauge). The impure R-365mfc contains 0.08% R-1354mzy plus other impurities. One stream contains impure R-365mfc while the second contains chlorine. By blending the two streams the ratio of chlorine to R-1354mzy is varied. The radiation exposure is calculated from the residence time and the light intensity and varies from 2 to 3.5 watts-hour/kg. After exposure to the ultraviolet light the product stream is analyzed by gas chromatography using the procedures of Example 1.

It is observed that, as the molar ratio of chlorine to R-1354mzy is increased from 0.1 to about 1.5, the concentration of R-1354mzy, and of the other olefins is reduced from their feed concentrations to concentrations below the detection limit (10 ppm). In proportion to the decrease in R-1354mzy and the other olefins, the corresponding chlorinated products are observed to increase. At the molar ratio corresponding to an R-1354mzy concentration of about 100 ppm (i.e. a molar ratio near 1.0), the concentration of R-355mdc is observed to begin increasing with increasing molar ratio.

What is claimed is:

1. A process for removing 1,1,1,3-tetrafluoro-2-butene (R-1354mzy), and optionally other olefinic impurities, from 1,1,1,3,3-pentafluorobutane (R-365mfc) by photochlorination comprising (a) contacting a mixture consisting substantially of a predetermined weight amount of R-365mfc and up to about 20,000 wt. ppm R-1354mzy with about 1–5 mols of chlorine for each mol of R-1354mzy, and optionally other olefinic impurities, in the presence of ultraviolet light having wavelengths between about 300 and 400 nm providing an exposure greater than zero and at least about 0.02 watt-hour/kg of said mixture, at a temperature in the range of about −50° C. to 200° C., said photochlorination being effective to reduce the concentration in the mixture of R-1354mzy, and optionally other olefinic impurities, to less than 100 wt. ppm by converting said R-1354mzy to 2,3-dichloro-1,1,1,3-tetrafluorobutane (R-354) or other butane which contains greater amounts of chlorine, as at least about 96% of said predetermined weight amount of R-365mfc is maintained in the mixture; and (b) separating the R-354 or other butane formed in (a) from R-365mfc.

2. A process according to claim 1 wherein the boiling point of said R-354 or other butane is at least about 40° C. above the boiling point of said R-365mfc and separating the R-365mfc and the R-354 or other butane by distillation.

3. The process of claim 1 effected as a batch process.

4. The process of claim 1 wherein said ultraviolet light provides an exposure of about 0.02 to 2 watts-hour/kg of said mixture.

5. The process of claim 1 wherein about 1 to about 1.5 mols of chlorine are present for each mol of R-1354mzy.

6. The process of claim 1 wherein the contacting of (a) is carried out at a temperature and a pressure sufficient to assure that R-365mfc is liquid.

7. The process of claim 1 wherein the contacting of (a) is carried out at a temperature and a pressure at which R-365mfc is vapor.

8. The process of claim 1 wherein the temperature is in the range of about 25° C. to 60° C.

9. The process of claim 1 wherein the separation of (b) is carried out by distillation.

10. The process of claim 1 wherein said other olefinic impurities comprise R-1353.

11. The process of claim 1 effected as a continuous process.

* * * * *